(12) United States Patent
Ahn

(10) Patent No.: US 12,245,943 B1
(45) Date of Patent: Mar. 11, 2025

(54) METHOD OF MANUFACTURING SPINAL CAGE FOR IMPROVING BONE UNION RATE

(71) Applicants: GBS Commonwealth Co., Ltd., Seoul (KR); PMT Republic, Inc., Walnut, CA (US)

(72) Inventor: Kyoung Gee Ahn, Seoul (KR)

(73) Assignees: GBS Commonwealth Co., Ltd., Seoul (KR); PMT Republic, Inc., Walnut, CA (US)

(*) Notice: Subject to any disclaimer, the term of this patent is extended or adjusted under 35 U.S.C. 154(b) by 0 days.

(21) Appl. No.: 18/642,828

(22) Filed: Apr. 23, 2024

(30) Foreign Application Priority Data

Feb. 26, 2024 (KR) .................. 10-2024-0027483

(51) Int. Cl.
| | | |
|---|---|---|
| C23C 14/02 | (2006.01) | |
| A61F 2/30 | (2006.01) | |
| A61F 2/44 | (2006.01) | |
| A61L 27/18 | (2006.01) | |
| A61L 27/30 | (2006.01) | |
| C23C 14/20 | (2006.01) | |

(52) U.S. Cl.
CPC .......... *A61F 2/3094* (2013.01); *A61F 2/4455* (2013.01); *A61L 27/18* (2013.01); *A61L 27/306* (2013.01); *C23C 14/021* (2013.01); *C23C 14/028* (2013.01); *C23C 14/205* (2013.01); *A61F 2310/00407* (2013.01); *A61F 2310/00592* (2013.01); *A61L 2420/02* (2013.01); *A61L 2430/38* (2013.01)

(58) Field of Classification Search
CPC ... C23C 14/021; C23C 14/028; C23C 14/205; A61F 2/3094; A61F 2/4455; A61F 2310/00407; A61F 2310/00592; A61L 27/18; A61L 27/306; A61L 2420/02; A61L 2430/38
USPC ........................................ 204/192.12, 192.15
See application file for complete search history.

(56) References Cited

FOREIGN PATENT DOCUMENTS

JP 11-320745 * 11/1999
WO WO2019/078455 A1 * 4/2019

OTHER PUBLICATIONS

Taherian et al. Optimum Surface Roughness for Titanium-Coated PEEK Produced by Electron Beam PVD for Orthopedic Applications, Materials Technology, Advanced Performance Materials, Jan. 2021. (Year: 2021).*
Buck et al. "Surface Modification Strategies to Improve the Osseointegration of Poly(etheretherketone) and Its Composites", Macromolecular Bioscience, 2020, 20 pp. 1-26. (Year: 2020).*

(Continued)

*Primary Examiner* — Rodney G McDonald
(74) *Attorney, Agent, or Firm* — NKL Law; Jae Youn Kim

(57) ABSTRACT

Disclosed is a method of manufacturing a spinal cage for improving a bone union rate, including preparing a cage body to be processed including a polymer material, sanding the surface of the cage body roughly by spraying ceramic beads onto the surface of the cage body, and depositing a coating film with a metal material on the surface of the cage body, in which the metal material of the coating film has higher biocompatibility than the polymer material of the cage body, simultaneously achieving stability of the polymer material and high biocompatibility of the metal material.

17 Claims, 14 Drawing Sheets

(56) References Cited

OTHER PUBLICATIONS

Banghard et al. "Plasma treatment on novel carbon fiber reinforced PEEK cages to enhance bioactivity", Current Directions in Biomedical Engineering 2016; 2(1) p. 569-572. (Year: 2016).*
Machine Translation WO2019/078455 A1 (Year: 2019).*
Machine Translation JP 11-320745 (Year: 1999).*

* cited by examiner

METHOD OF MANUFACTURING SPINAL CAGE FOR IMPROVING BONE UNION RATE

CROSS-REFERENCE TO RELATED APPLICATIONS

This U.S. non-provisional patent application claims priority under 35 U.S.C. § 119 of Korean Patent Application No. 10-2024-0027483, filed on Feb. 26, 2024, the entire contents of which are hereby incorporated by reference.

BACKGROUND OF THE INVENTION

Field of the Invention

The present invention relates to a method of manufacturing a spinal cage, and more particularly to a method of manufacturing a spinal cage for improving a bone union rate.

Description of the Related Art

The spine may have structural problems, such as problems with stable alignment or narrowing of the gap between vertebral bodies, for various reasons such as congenital or degenerative disorders, or accidents.

Representative examples of spinal disease include spinal anomaly, spinal fracture, spinal disc herniation, spinal stenosis, facet hypertrophy, and the like. This spinal disease requires surgical treatment when symptoms worsen and conservative treatment becomes difficult.

Among surgical treatment methods, spinal fusion is a procedure of removing the intervertebral disc in which spinal disease has occurred, inserting a spinal cage between the vertebral bodies to create a space for the bone to grow into for fusion, reducing pain by increasing the gap between the vertebral bodies, and maintaining spinal stability by restoring the lordosis of the spine.

In general, the spinal cage used in spinal fusion has a hollow therein, and a bone chip is inserted therein. As the bone chip regenerates, bone fusion occurs between the upper and lower vertebral bodies.

Various types of spinal cages have been developed depending on the surgical method, and various shapes are being developed to restore biomechanical stability of the spine while being implantable in the human body.

However, conventional spinal cages made of polymer materials have similar strength to vertebral bodies and cortical bones, providing stability, but have the disadvantage of inferior bone union properties (biocompatibility).

Meanwhile, conventional spinal cages made of metal materials have superior bone union properties, but are problematic in that facing surfaces of adjacent vertebral bodies are lowered by the top and bottom surfaces of the spinal cage after completion of the spinal fusion procedure.

The matters described in the related art are only for improving understanding of the background of the present invention, and should not be taken as an acknowledgment that they correspond to conventional techniques already known to those of ordinary skill in the art.

SUMMARY OF THE INVENTION

The present invention has been made keeping in mind the problems encountered in the related art, and an object of the present invention is to provide a method of manufacturing a spinal cage for improving a bone union rate capable of simultaneously achieving stability of a polymer material and high biocompatibility of a metal material.

In addition, another object of the present invention is to provide a method of manufacturing a spinal cage for improving a bone union rate, which may further increase biocompatibility by increasing the surface roughness value of the spinal cage without deteriorating performance of a metal material coating.

The technical problems to be achieved by the present invention are not limited to the foregoing, and other technical problems not mentioned herein may be clearly understood by those skilled in the art from the description of the present invention.

In order to accomplish the above objects, the present invention provides a method of manufacturing a spinal cage for improving a bone union rate, including preparing a cage body to be processed including a polymer material, sanding a surface of the cage body roughly by spraying ceramic beads onto the surface of the cage body, and depositing a coating film with a metal material on the surface of the cage body, in which the metal material of the coating film has higher biocompatibility than the polymer material of the cage body.

In the method of manufacturing a spinal cage for improving a bone union rate according to an embodiment of the present invention, the polymer material of the cage body may be polyether ether ketone (PEEK).

In the method of manufacturing a spinal cage for improving a bone union rate according to an embodiment of the present invention, the metal material of the coating film may be titanium or a titanium alloy.

The method of manufacturing a spinal cage for improving a bone union rate according to an embodiment of the present invention may further include washing the cage body using a neutral detergent containing a surfactant component before processing, after preparing the cage body.

In the method of manufacturing a spinal cage for improving a bone union rate according to an embodiment of the present invention, the ceramic beads used in sanding the surface of the cage body may be round ceramic beads.

In the method of manufacturing a spinal cage for improving a bone union rate according to an embodiment of the present invention, a particle size of the ceramic beads may be 0.1 to 600 μm.

The method of manufacturing a spinal cage for improving a bone union rate according to an embodiment of the present invention may include, after sanding the surface of the cage body, subjecting the cage body to first washing using a predetermined washing solution, subjecting the cage body to second washing in distilled water at a predetermined temperature, and subjecting the cage body to third washing using a predetermined washing solution.

In the method of manufacturing a spinal cage for improving a bone union rate according to an embodiment of the present invention, the washing solution used in the first washing may include 100 parts by weight of distilled water and 10 to 50 parts by weight of acetone.

In the method of manufacturing a spinal cage for improving a bone union rate according to an embodiment of the present invention, a temperature of the distilled water used in the second washing may be 20 to 90° C.

In the method of manufacturing a spinal cage for improving a bone union rate according to an embodiment of the present invention, the washing solution used in the third washing may include 100 parts by weight of distilled water and 10 to 50 parts by weight of acetone.

The method of manufacturing a spinal cage for improving a bone union rate according to an embodiment of the present invention may include, after the third washing, subjecting the cage body to fourth washing using ultrasonic waves in a washing water tank containing an alkaline solution, subjecting the cage body to fifth washing by spraying ultrapure water, and subjecting the cage body to sixth washing in a washing water tank containing ultrapure water.

In the method of manufacturing a spinal cage for improving a bone union rate according to an embodiment of the present invention, the fourth washing may be performed at a temperature of 10 to 90° C. for 9 minutes.

In the method of manufacturing a spinal cage for improving a bone union rate according to an embodiment of the present invention, the fifth washing may be performed at a temperature of 10 to 90° C. for 15 minutes.

In the method of manufacturing a spinal cage for improving a bone union rate according to an embodiment of the present invention, the sixth washing may be performed at a temperature of 10 to 90° C. for 6 minutes.

The method of manufacturing a spinal cage for improving a bone union rate according to an embodiment of the present invention may further include, after the sixth washing, drying the cage body at a temperature of 60 to 120° C. for 8 minutes.

In the method of manufacturing a spinal cage for improving a bone union rate according to an embodiment of the present invention, a thickness of the coating film deposited on the surface of the cage body may be 0.1 to 10 μm.

In the method of manufacturing a spinal cage for improving a bone union rate according to an embodiment of the present invention, depositing the coating film may include disposing cage bodies on a rotating unit rotatably provided in a chamber, disposing a metal target made of a metal material at a distance from the cage bodies in the chamber, injecting an inert gas into the chamber through a gas supply unit, and coating surfaces of the cage bodies with the metal material by applying a predetermined temperature and pressure to an inside of the chamber and applying a predetermined voltage to the metal target.

In the method of manufacturing a spinal cage for improving a bone union rate according to an embodiment of the present invention, in disposing the cage bodies, the cage bodies may be spaced apart from each other at regular intervals in both longitudinal and transverse directions in the chamber.

In the method of manufacturing a spinal cage for improving a bone union rate according to an embodiment of the present invention, coating the surfaces of the cage bodies may be performed at a pressure of $3*10^{-3}$ to $7*10^{-3}$ torr, a temperature of 100 to 300° C., a power of 20 kW, and a voltage of 5 to 30 V.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
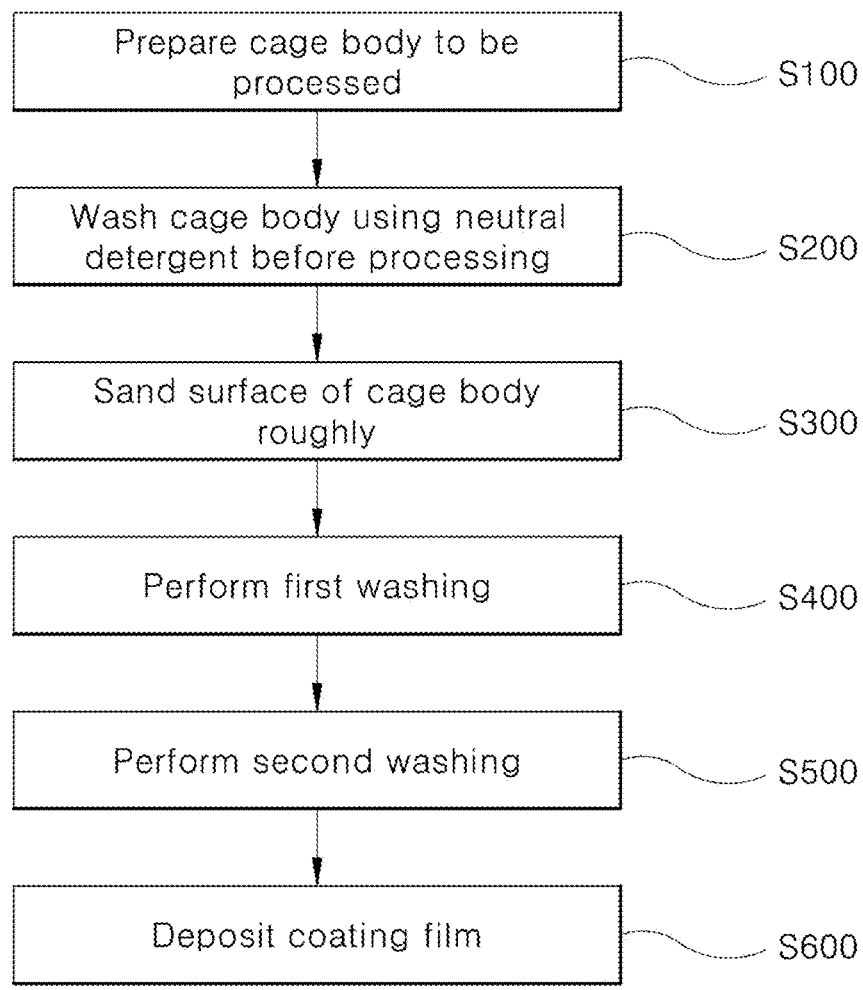
FIG. 1 is a flowchart showing a process of manufacturing a spinal cage for improving a bone union rate according to an embodiment of the present invention.

Hereinafter, a detailed description will be given of the present invention in conjunction with the accompanying drawings so that those of ordinary skill in the art may easily implement the present invention. However, the present invention may be embodied in a variety of different forms and is not limited to the embodiments described herein.

In order to clearly explain the present invention, parts irrelevant to the description are omitted, and the same reference numerals are assigned to the same or similar elements throughout the specification.

In addition, the terms or words used in the present specification and claims should not be construed as being limited to the ordinary or dictionary meanings, and should be understood as having meanings and concepts consistent with the technical spirit of the present invention based on the principle that the inventor may appropriately define the concepts of terms in order to explain the invention in the best way.

Figure 2:
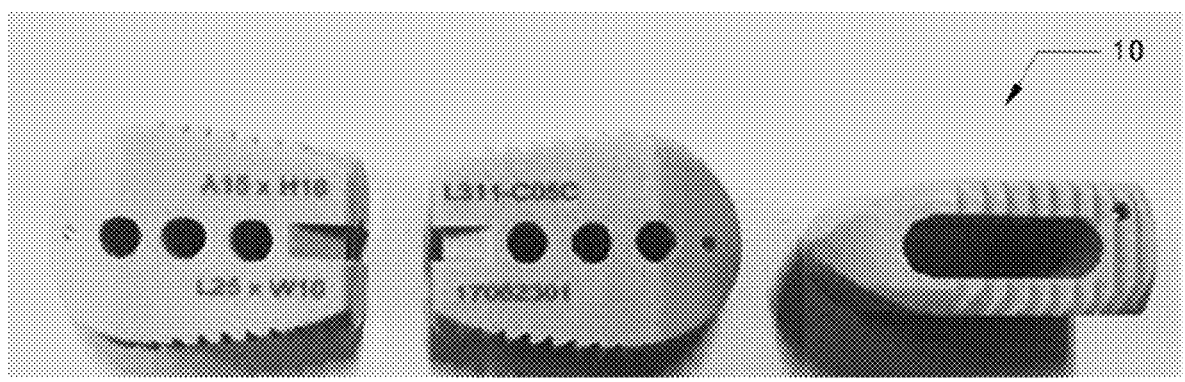
FIG. 2 shows the cage body before depositing a coating film according to an embodiment of the present invention.
Figure 3:
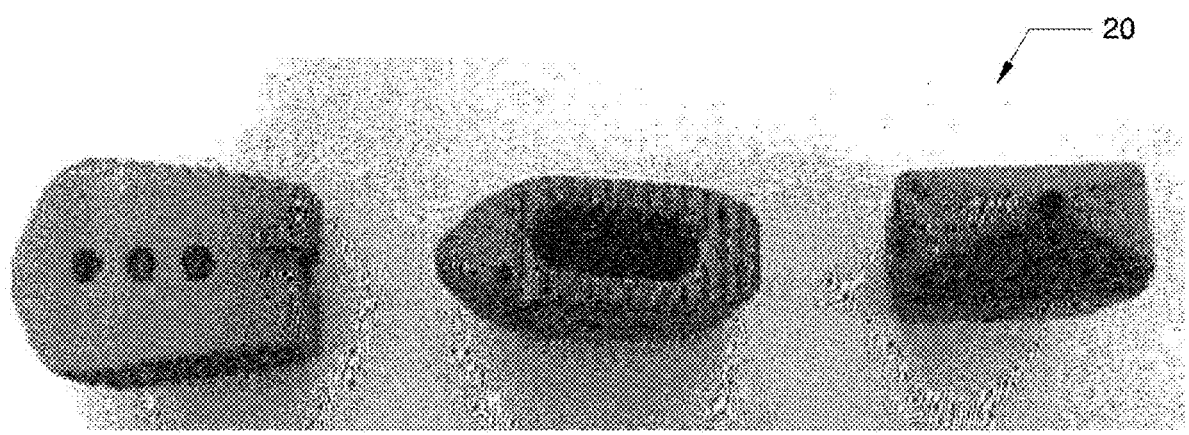
FIG. 3 shows the cage body after depositing the coating film according to an embodiment of the present invention.

FIG. 1 is a flowchart showing a process of manufacturing a spinal cage for improving a bone union rate according to an embodiment of the present invention, FIG. 2 shows the cage body before depositing a coating film according to an embodiment of the present invention, FIG. 3 shows the cage body after depositing the coating film according to an embodiment of the present invention.

As shown in the drawing, the method of manufacturing a spinal cage according to the present invention includes preparing a cage body to be processed including a polymer material (S100), sanding the surface of the cage body roughly by spraying ceramic beads onto the surface of the cage body (S300), and depositing a coating film with a metal material on the surface of the cage body (S600).

The cage body 10 is a medical device used in spinal fusion, and is inserted between the vertebral bodies to maintain the gap between the vertebral bodies and create a space for the bone to grow into for fusion.

A hollow is formed in the central portion of the cage body 10, and this hollow is filled with autograft, allograft, or synthetic bone to promote bone growth.

In the illustrated embodiment, the cage body 10 is formed in a bullet shape that is long in the front-rear direction, but the present invention is not limited thereto and the cage body may be formed in various shapes such as a flat shape, a curved shape, a disc shape, and the like. The cage body 10 may be manufactured using an SLM (selective laser melting)-type 3D printer.

The cage body 10 may include a polymer material as a main component of the cage body 10, and may also include various additives or fillers.

The polymer material constituting the cage body 10 is preferably polyether ether ketone (PEEK).

Polyether ether ketone (PEEK) is a high-performance thermoplastic resin that has mechanical strength and superior chemical resistance at high temperatures and has excellent tensile properties. In particular, polyether ether ketone (PEEK) has similar strength to vertebral bodies, so it may provide stability when used as the cage body 10.

The coating film 20 deposited on the surface of the cage body 10 is made of a metal material having higher biocompatibility than the polymer material of the cage body 10. For example, the metal material of the coating film 20 is preferably titanium or a titanium alloy.

Titanium is fairly light, weighing equal to or less than half as much as steel, does not rust, and has low thermal and electrical conductivity. A titanium alloy has high specific strength, and exhibits excellent wear resistance and highest corrosion resistance among stainless steel alloys. In particular, titanium or a titanium alloy has high biocompatibility and is therefore suitable for use as a spinal cage.

In the present invention, the coating film 20 may be deposited using a metal material such as titanium or a titanium alloy on the surface of the cage body 10 made of a polymer material such as polyether ether ketone (PEEK), thereby simultaneously achieving stability of the polymer material and high biocompatibility of the metal material.

Figure 4:
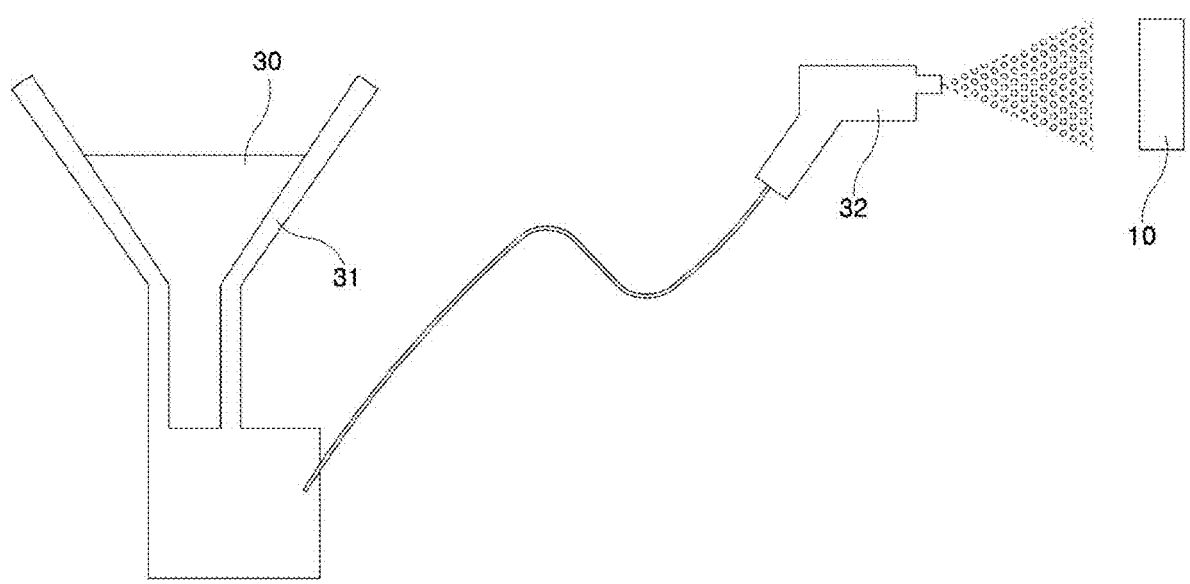
FIG. 4 shows a sanding process according to an embodiment of the present invention.

FIG. 4 shows a sanding process according to an embodiment of the present invention.

The method of the present invention may further include washing the cage body using a neutral detergent containing a surfactant component (S200), after preparing the cage body (S100) and before sanding the surface of the cage body (S300).

In preparing the cage body (S100), processing oil may be left behind on the surface of the cage body 10 during processing. If this processing oil is not completely removed, deposition performance of the coating film 20 may remarkably deteriorate in the subsequent deposition process (S600), so processing oil must be removed through washing.

Washing the cage body (S200) before processing is performed using a neutral detergent containing a surfactant component. A surfactant is a material that is activated at the contact surface between materials having different properties, and is used to wash the surface of the cage body 10.

Sanding the surface of the cage body (S300) may include processing the surface of the cage body 10 roughly by spraying ceramic beads 30 onto the surface of the cage body 10, thereby increasing the surface roughness value of the cage body 10, which may further increase biocompatibility.

As shown in the drawing, sanding the surface of the cage body (S300) may include filling the inside of a sanding case 31 with ceramic beads 30 and spraying the ceramic beads through a nozzle 32 with high-pressure compressed air to roughen the surface of the cage body 10.

Here, the ceramic beads 30 used in sanding the surface of the cage body (S300) are preferably round ceramic beads.

Beads used in a conventional sanding process are generally made of sharp metal materials. However, when the cage body 10 made of a polymer material is subjected to sanding (S300) using sharp beads, the beads may become embedded in the surface of the cage body 10, making it difficult to remove the beads, and it may be dangerous if the beads enter the human body. Hence, round ceramic beads 30 are used.

Moreover, the particle size of the ceramic beads 30 used in sanding the surface of the cage body (S300) is preferably 0.1 to 600 μm. In general, as the surface roughness value of the cage body 10 increases, the bone union rate (biocompatibility) increases. However, if the surface roughness value is excessively high, performance of coating deposition may decrease.

Therefore, in the present invention, the ceramic beads 30 have a particle size suitable for maximizing biocompatibility without deteriorating coating performance. If the particle size of the ceramic beads 30 is less than 0.1 μm, the surface roughness value may be too low and biocompatibility may remarkably decrease, whereas if the particle size of the ceramic beads 30 exceeds 600 μm, the surface roughness value may be too high, remarkably impairing performance of deposition of the coating film 20.

Figure 5:
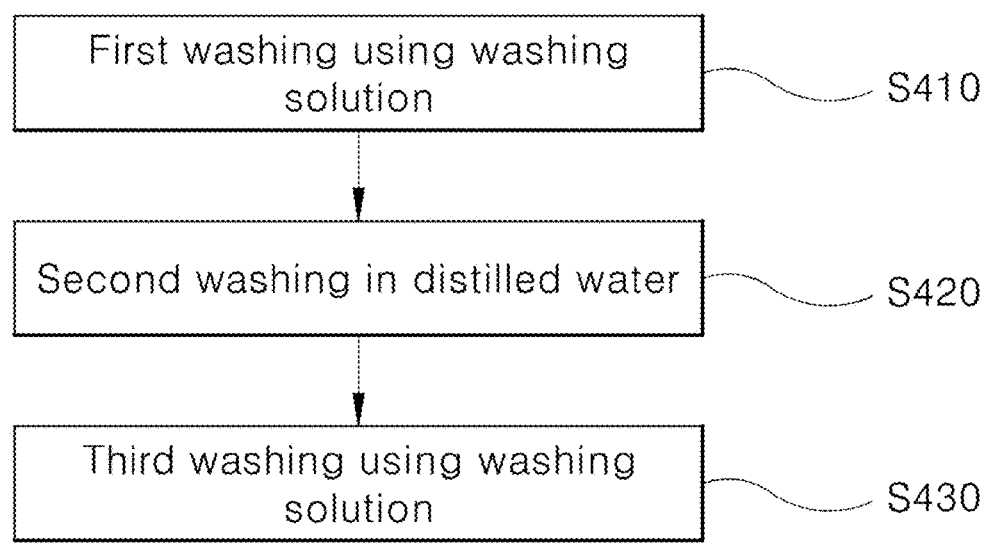
FIG. 5 is a flowchart showing a first washing process according to an embodiment of the present invention.
Figure 6:
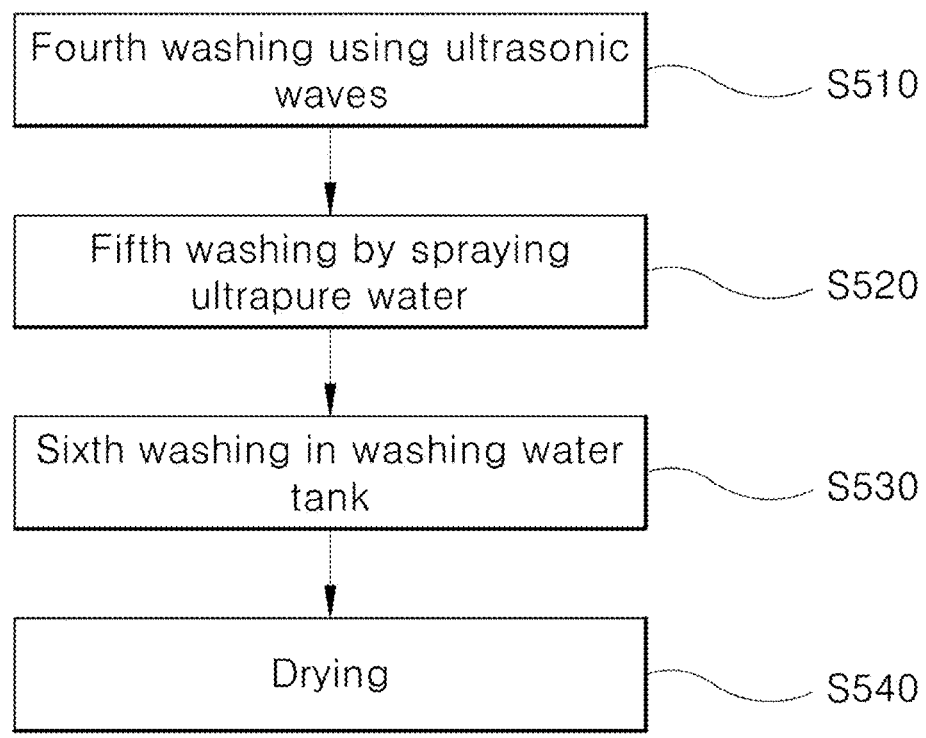
FIG. 6 is a flowchart showing a second washing process according to an embodiment of the present invention.

FIG. 5 is a flowchart showing a first washing process according to an embodiment of the present invention, and FIG. 6 is a flowchart showing a second washing process according to an embodiment of the present invention.

As shown in the drawings, after sanding the surface of the cage body roughly (S300), the first washing process (S400) and the second washing process (S500) are performed to remove the remaining ceramic beads 30 from the cage body 10.

Specifically, the first washing process (S400) includes subjecting the cage body to first washing using a predetermined washing solution (S410), subjecting the cage body to second washing in distilled water at a predetermined temperature (S420), and subjecting the cage body to third washing using a predetermined washing solution (S430).

The first washing (S410) is performed for about 5 minutes using a washing solution including 100 parts by weight of distilled water and 10 to 50 parts by weight of acetone.

The second washing (S420) is performed for about 5 minutes using 100% distilled water at a temperature of 20 to 90° C.

The third washing (S430) is performed for about 5 minutes using a washing solution including 100 parts by weight of distilled water and 10 to 50 parts by weight of acetone.

When performing the first washing process (S400) in this way, the ceramic beads 30 remaining on the surface of the cage body 10 may be removed to some extent, and the second washing process (S500) is subsequently performed.

Specifically, the second washing process (S500) includes subjecting the cage body to fourth washing using ultrasonic waves in a washing water tank containing an alkaline solution (S510), subjecting the cage body to fifth washing by spraying ultrapure water (S520), and subjecting the cage body to sixth washing in a washing water tank containing ultrapure water (S530).

The fourth washing (S510) is performed using ultrasonic waves at a temperature of 10 to 90° C. for about 9 minutes. In the fourth washing (S510), an ultrasonic vibrator (not shown) is installed in the washing water tank to generate vibration, and the generated vibration is transmitted to the alkaline solution to disperse the ceramic beads 30 on the surface of the cage body 10. The alkaline solution contained in the washing water tank may include sodium hydroxide, sodium carbonate, sodium silicate, sodium phosphate, or sodium cyanide.

The fifth washing (S520) is performed using ultrapure water at a temperature of 10 to 90° C. for about 15 minutes. As used herein, the term "ultrapure water" refers to distilled water with electrical conductivity, number of solid particles, number of viable bacteria, organic matter, etc. suppressed to extremely low values, and more specifically, the number of particles with a diameter of 0.1 μm or less per $cm^3$ may be 20 or less, and the number of viable bacteria per 100 $cm^3$ may be 1 or less.

The sixth washing (S530) is performed using ultrapure water at a temperature of 10 to 90° C. for about 6 minutes. In the sixth washing (S530), the cage body 10 may be washed with high-temperature ultrapure water to remove the ceramic beads 30 from the surface thereof, and subsequent drying (S540) may be performed more easily.

The second washing process (S500) may further include drying the cage body at a temperature of 60 to 120° C. for about 8 minutes (S540) after the sixth washing (S530). After completion of the drying (S540), the cage body 10 is transferred to a deposition device to perform the deposition process (S600).

Figure 7:
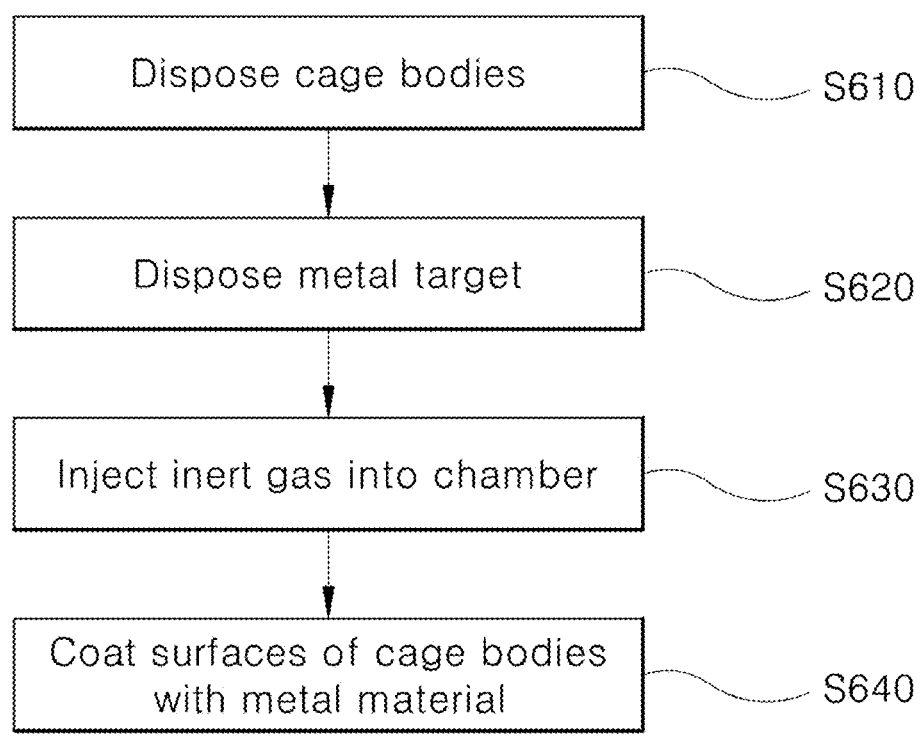
FIG. 7 is a flowchart showing a deposition process according to an embodiment of the present invention.
Figure 8:
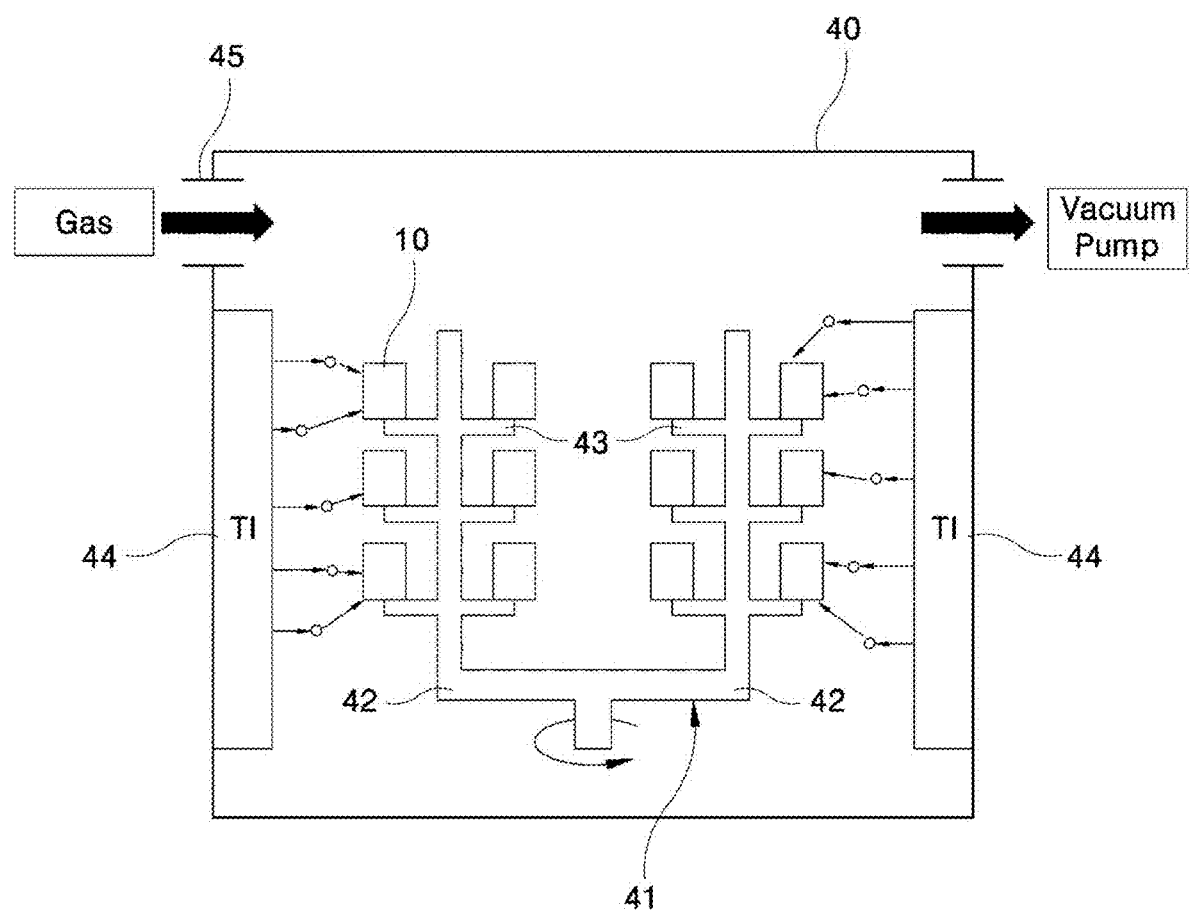
FIG. 8 shows the deposition process according to an embodiment of the present invention.

FIG. 7 is a flowchart showing the deposition process according to an embodiment of the present invention, and FIG. 8 shows the deposition process according to an embodiment of the present invention.

As shown in the drawing, a coating film 20 is deposited with a metal material on the surface of the cage body 10 (S600) after completion of the first washing process (S400) and the second washing process (S500).

The thickness of the coating film 20 deposited on the surface of the cage body 10 is preferably 0.1 to 10 μm. If the thickness of the coating film 20 is less than 0.1 μm, there may be a very high possibility that the coating is not properly performed, and the coating film 20 may melt and disappear too quickly. On the other hand, if the thickness of the coating film 20 exceeds 10 μm, adhesive strength may remarkably decrease, and the coating film 20 may be projected on the screen when X-ray is projected, which may cause confusion in medical treatment.

Depositing the coating film (S600) may include disposing cage bodies on a rotating unit rotatably provided in a chamber (S610), disposing a metal target made of a metal material at a distance from the cage bodies in the chamber (S620), injecting an inert gas into the chamber through a gas supply unit (S630), and coating the surfaces of the cage bodies with the metal material by applying a predetermined temperature and pressure to an inside of the chamber and applying a predetermined voltage to the metal target (S640).

As shown in the drawing, a deposition device configured to perform depositing the coating film (S600) includes a chamber 40, a rotating unit 41, a metal target 44, etc. The chamber 40 has a space therein so that various parts may be placed, and the rotating unit 41 is provided rotatably at the center of the inside of the chamber 40.

As such, the rotating unit 41 includes a pair of longitudinal supports 42 rotatably disposed on both sides about the rotation axis and a plurality of transverse supports 43 disposed perpendicular to individual longitudinal supports 42. The transverse supports 43 are vertically spaced apart from each other while being perpendicular to the longitudinal supports 42, and the intervals between the transverse supports 43 are preferably the same. The cage bodies 10 may be disposed on respective transverse supports 43.

In the present invention, the cage bodies 10 may be rotated in a state of being spaced apart from each other at regular intervals in both the longitudinal and transverse directions inside the chamber 40. Accordingly, when depositing the coating film 20, the coating film 20 may be uniformly deposited on the surfaces of the cage bodies 10.

The metal target 44 is spaced apart from the rotating unit 41 and attached to the inner surface of the chamber 40, and a metal material is supplied to the cage body 10 by applying a voltage thereto. The gas supply unit 45 supplies an inert gas into the chamber 40. Argon gas, etc. may be used as the inert gas.

In the coating process (S640), when a predetermined temperature and pressure are applied to the inside of the chamber 40 and a predetermined voltage is applied to the metal target 44, ions of the inert gas are accelerated and collide with the metal target 44, and the metal material (e.g., titanium) that is separated due to such collision adheres to the cage body 10, so that the coating film 20 is deposited.

Here, the coating process (S640) is preferably performed at a pressure of $3*10^{-3}$ to $7*10^{-3}$ torr, a temperature of 100 to 300° C., a power of 20 kW, and a voltage of 5 to 30 V.

If the pressure applied in the coating process (S640) is less than $3*10^{-3}$ torr, the time for which the deposition process is performed may excessively increase, whereas if the pressure applied in the coating process (S640) exceeds $7*10^{-3}$ torr, deposition efficiency of the coating film 20 may decrease.

If the temperature applied in the coating process (S640) is lower than 100° C., the temperature may be too low to perform the deposition process, whereas if the temperature applied in the coating process (S640) is higher than 300° C., the melting point of polyether ether ketone (PEEK) constituting the cage body 10 is about 341° C., and thus a possibility of damage to the cage body 10 may remarkably increase.

If the voltage applied in the coating process (S640) is less than 5 V, the ions of the inert gas in the chamber 40 may not receive sufficient force, making it difficult to separate the metal material despite collision of such ions with the metal target 44, whereas if the voltage applied in the coating process (S640) exceeds 30 V, the ions of the inert gas in the chamber 40 may penetrate in the metal target 44, rather than the metal material being separated due to collision thereof with the metal target 44.

Figure 9:
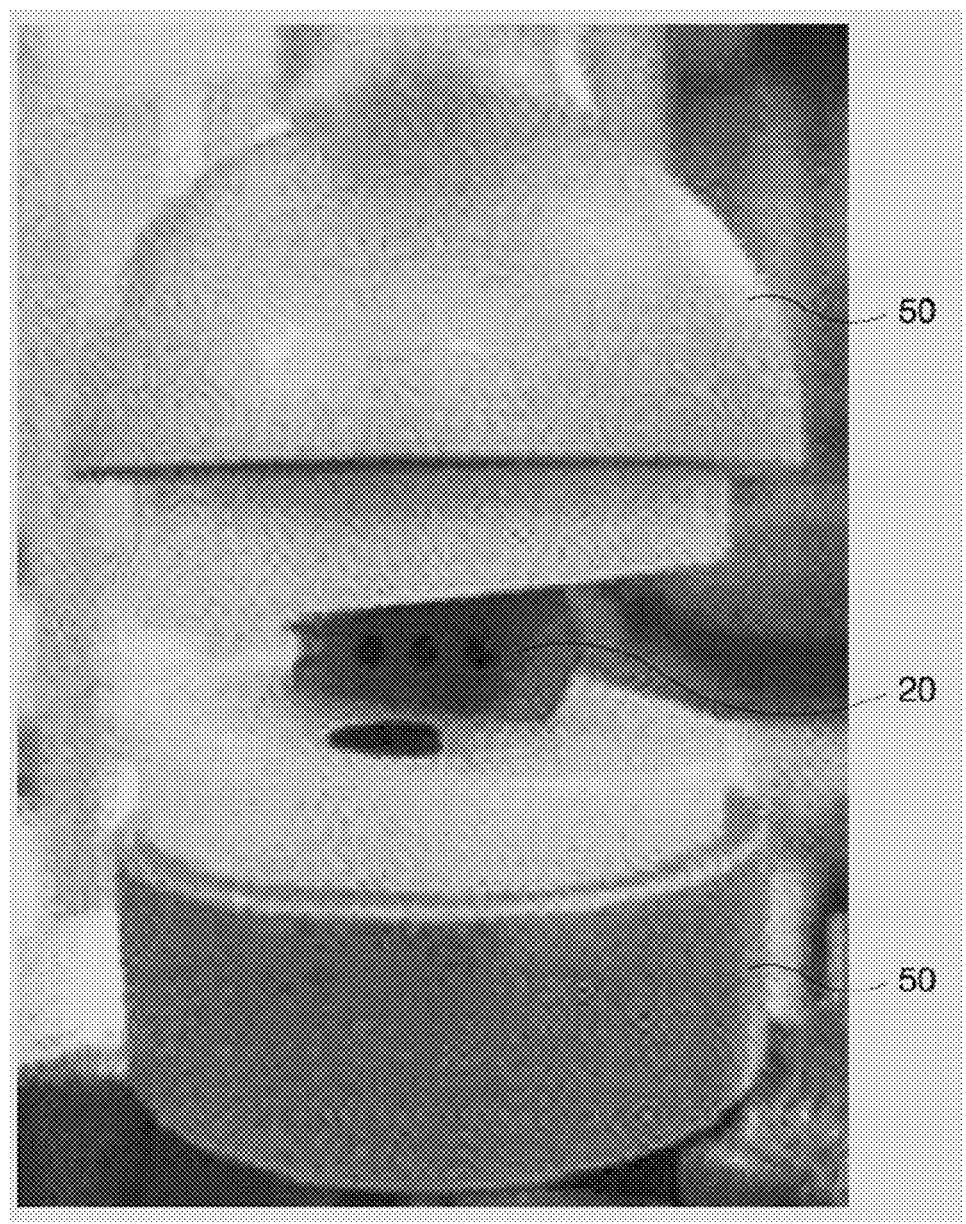
FIG. 9 shows a performance verification test of a cage body with a coating film deposited thereon according to an embodiment of the present invention.
Figure 10:
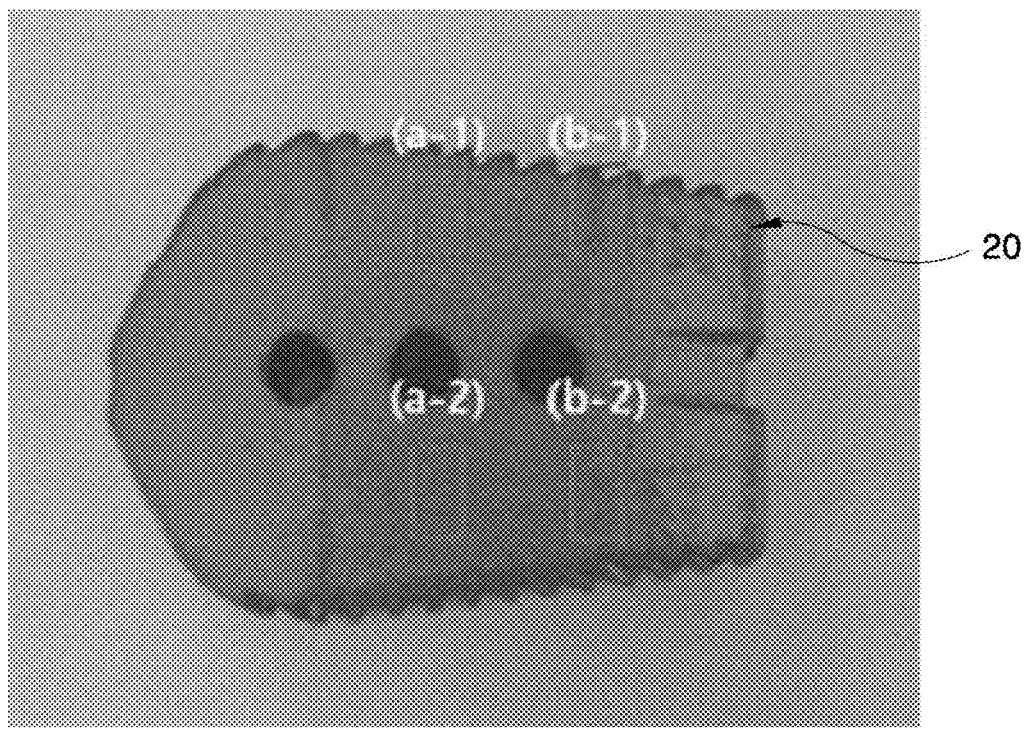
FIG. 10 shows the cage body after a performance verification test on the cage body with the coating film deposited thereon according to an embodiment of the present invention.
Figure 11:
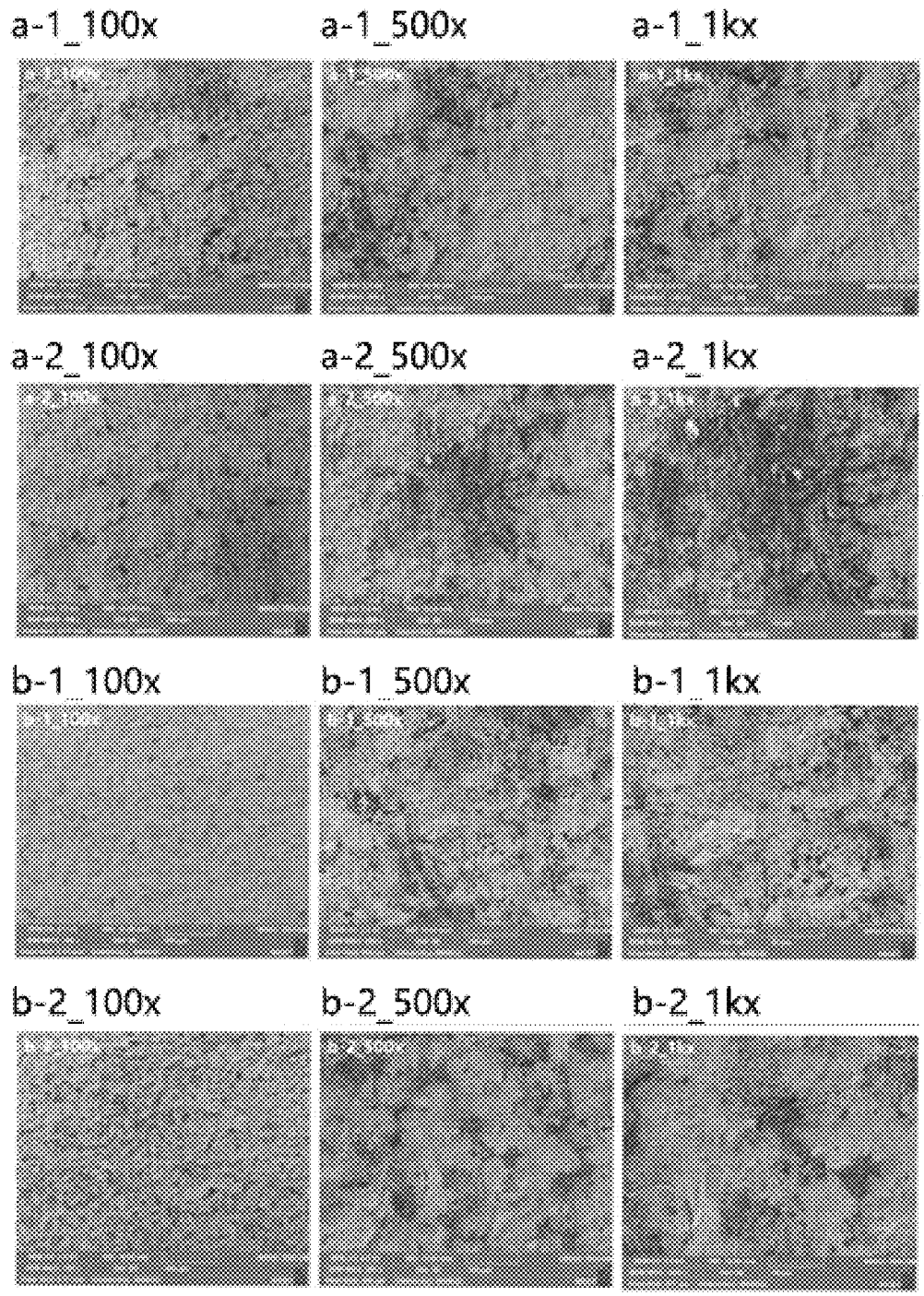
FIG. 11 shows enlarged images of contact portions between the jigs and the cage body after a performance verification test on the cage body with the coating film deposited thereon according to an embodiment of the present invention.
Figure 12:
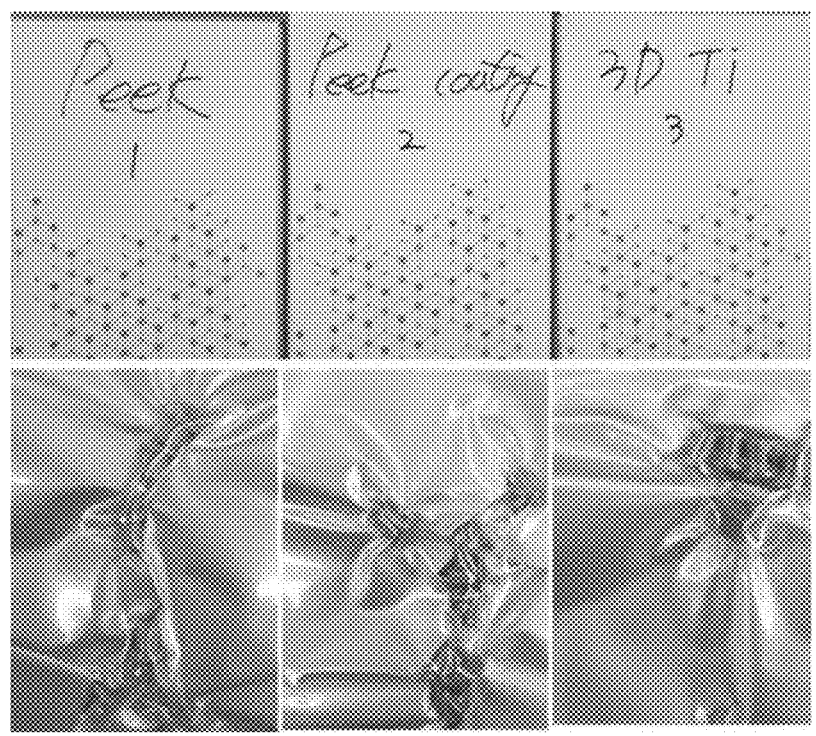
FIG. 12 shows specimens manufactured for animal testing of the cage body with the coating film deposited thereon according to an embodiment of the present invention.
Figure 13:
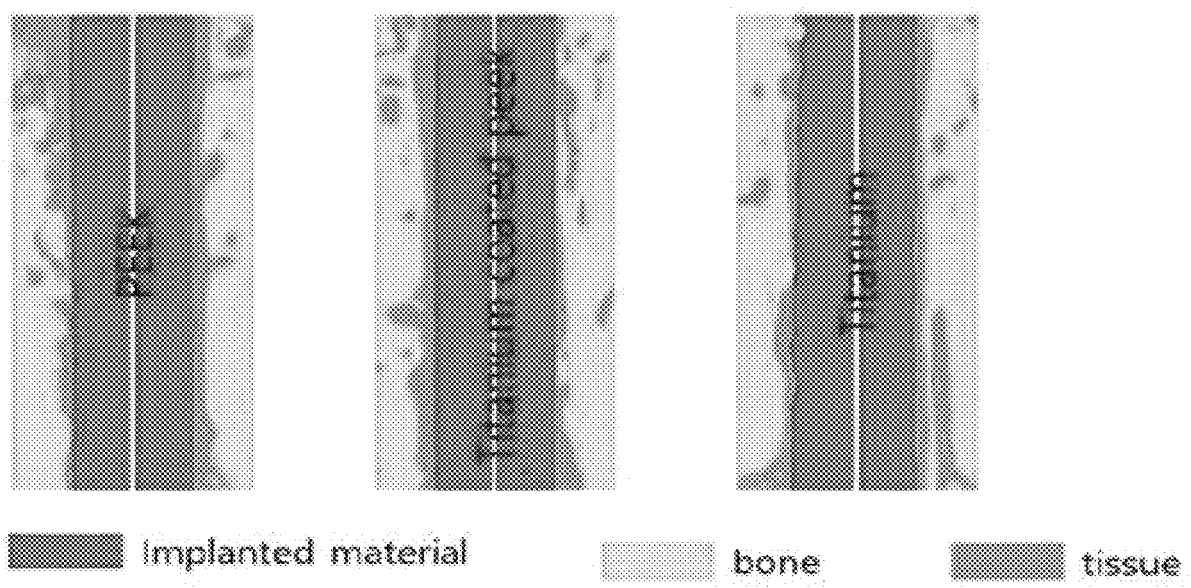
FIG. 13 shows microscope images of tissue that is collected and stained after animal testing of the cage body with the coating film deposited thereon according to an embodiment of the present invention.
Figure 14:
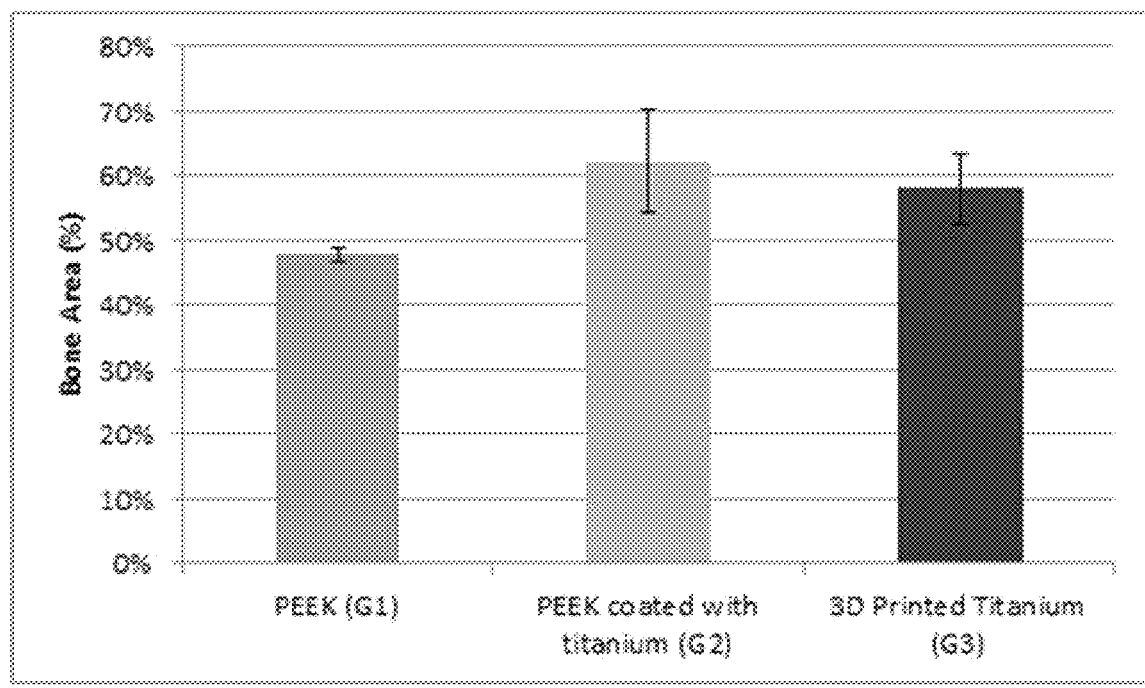
FIG. 14 is a graph comparing the bone area after animal testing of the cage body with the coating film deposited thereon according to an embodiment of the present invention.

FIG. 9 shows a performance verification test of the cage body with the coating film deposited thereon according to an embodiment of the present invention, FIG. 10 shows the cage body after a performance verification test on the cage body with the coating film deposited thereon according to an embodiment of the present invention, FIG. 11 shows enlarged images of contact portions between the jigs and the cage body after a performance verification test on the cage body with the coating film deposited thereon according to an embodiment of the present invention, FIG. 12 shows specimens manufactured for animal testing of the cage body with the coating film deposited thereon according to an embodiment of the present invention, FIG. 13 shows microscope images of tissue that is collected and stained after animal testing of the cage body with the coating film deposited thereon according to an embodiment of the present invention, and FIG. 14 is a graph comparing the bone area after animal testing of the cage body with the coating film deposited thereon according to an embodiment of the present invention.

As shown in FIGS. 9 to 11, after manufacturing the cage body 10 with the coating film 20 deposited thereon according to an embodiment of the present invention, a fatigue test is performed to verify the stability of the product.

In the stability verification test, as shown in FIG. 9, jigs 50 are placed on the top and bottom of the cage body 10 and a load is repetitively applied 5 million times to determine whether debris or particles are generated on the surface of the cage body 10.

The stability verification test is conducted using field emission-scanning electron microscopy (FE-SEM), and as shown in FIG. 10, the contact portions a-1, a-2, b-1, b-2 between the jigs 50 and the cage body 10 are analyzed.

As shown in FIG. 11, based on results of FE-SEM of the contact portions between the jigs 50 and the cage body 10, it can be confirmed that there is no peeling or detachment of the coating film 20.

As shown in FIGS. 12 to 14, after manufacturing the cage body 10 with the coating film 20 deposited thereon according to an embodiment of the present invention, animal testing is performed to compare bone union rates. In animal testing, a specimen is manufactured and implanted into the leg bone of a rabbit, and the extent to which the bone is attached to the surface of the cage body 10 is determined.

As shown in FIG. 12, three specimens are prepared. In the drawing, the leftmost specimen is a polyether ether ketone (PEEK) specimen, the middle specimen is a specimen in which the coating film 20 is deposited on the surface of the cage body 10 according to an embodiment of the present invention, and the rightmost specimen is a titanium specimen.

Each of three sterilized specimens thus prepared is implanted in the femur of a 4-month-old male rabbit (New Zealand white rabbit), and after a 12-week recovery period, each specimen is extracted and the extent of bone formation around the specimen is analyzed.

FIG. 13 shows microscope images of tissue that is collected and stained 12 weeks after implanting each specimen into the femur of a rabbit. In the drawing, the leftmost image is an image of the polyether ether ketone (PEEK) specimen, the middle image is an image of the specimen of the cage body 10 with the coating film 20 deposited thereon according to an embodiment of the present invention, and the rightmost image is an image of the titanium specimen.

As shown in the drawing, it can be confirmed that the specimen of the cage body 10 with the coating film 20 deposited thereon according to an embodiment of the present invention has a larger amount of newly generated bone, and also that tissue is in good contact with no gaps between the surface of the specimen (titanium coated peek) and the newly generated bone.

More specifically, as shown in FIG. 14, based on results of measurement of the bone formation rate (bone area) in the selected area by analyzing the microscope images, the bone area is determined to be much higher in the specimen (G2) with the titanium coating film 20 deposited thereon according to an embodiment of the present invention than in the polyether ether ketone (PEEK) specimen without any coating (G1).

In this way, the coating film 20 is deposited with a metal material on the surface of the cage body 10 including a polymer material in the present invention, thereby applying the advantages of stability of physical properties of the polymer material and high biocompatibility of the metal material to a spinal cage.

As is apparent from the above description, the present invention has the effect of applying the advantages of stability of physical properties of a polymer material and high biocompatibility of a metal material to a spinal cage by depositing a coating film with a metal material on the surface of a cage body including a polymer material.

In addition, the present invention has the effect of further increasing biocompatibility without deteriorating performance of the coating film by increasing the surface roughness value of a cage body by a sanding process.

Furthermore, the present invention has the effect of remarkably enhancing adhesion between different materials by depositing a coating film with a metal material on the surface of the cage body under optimal conditions.

The present invention described above is not limited to the aforementioned embodiments and the appended drawings, and those skilled in the art will appreciate that various substitutions, modifications, and alterations are possible, without departing from the technical spirit of the present invention.

The invention claimed is:

1. A method of manufacturing a spinal cage for improving a bone union rate, comprising:
preparing a cage body to be processed comprising a polymer material;
sanding a surface of the cage body by spraying ceramic beads onto the surface of the cage body; and
subjecting the cage body to first washing using a predetermined washing solution;
subjecting the cage body to second washing in distilled water at a predetermined temperature; and
subjecting the cage body to third washing using another predetermined washing solution; and
depositing a coating film with a metal material on the surface of the cage body,
wherein the metal material of the coating film has higher biocompatibility than the polymer material of the cage body, and
wherein the predetermined washing solution used in the first washing comprises 100 parts by weight of distilled water and 10 to 50 parts by weight of acetone.

2. The method of claim 1, wherein the polymer material of the cage body is polyether ether ketone (PEEK).

3. The method of claim 1, wherein the metal material of the coating film is titanium or a titanium alloy.

4. The method of claim 1, further comprising washing the cage body using a neutral detergent containing a surfactant component before processing, after the preparing of the cage body.

5. The method of claim 1, wherein the ceramic beads used in the sanding of the surface of the cage body are round ceramic beads.

6. The method of claim 5, wherein a particle size of the ceramic beads is 0.1 to 600 μm.

7. The method of claim 1, wherein the predetermined temperature of the distilled water used in the second washing is 20 to 90° C.

8. The method of claim 1, wherein the another predetermined washing solution used in the third washing comprises 100 parts by weight of distilled water and 10 to 50 parts by weight of acetone.

9. The method of claim 1, comprising, after the third washing:
- subjecting the cage body to fourth washing using ultrasonic waves in a washing water tank containing an alkaline solution;
- subjecting the cage body to fifth washing by spraying water; and
- subjecting the cage body to sixth washing in a washing water tank containing water.

10. The method of claim 9, wherein the fourth washing is performed at a temperature of 10 to 90° C. for 9 minutes.

11. The method of claim 9, wherein the fifth washing is performed at a temperature of 10 to 90° C. for 15 minutes.

12. The method of claim 9, wherein the sixth washing is performed at a temperature of 10 to 90° C. for 6 minutes.

13. The method of claim 9, further comprising, after the sixth washing:
- drying the cage body at a temperature of 60 to 120° C. for 8 minutes.

14. The method of claim 1, wherein a thickness of the coating film deposited on the surface of the cage body is 0.1 to 10 μm.

15. The method of claim 1, wherein the cage body includes a plurality of cage bodies, and the depositing of the coating film comprises:
- disposing the plurality of cage bodies on a rotating unit rotatably provided in a chamber;
- disposing a metal target made of the metal material at a distance from the plurality of cage bodies in the chamber;
- injecting an inert gas into the chamber through a gas supply unit; and
- coating surfaces of the plurality of cage bodies with the metal material by applying a predetermined temperature and pressure to an inside of the chamber and applying a predetermined voltage to the metal target.

16. The method of claim 15, wherein, in the disposing of the plurality of cage bodies, the plurality of cage bodies are spaced apart from each other at regular intervals in both longitudinal and transverse directions in the chamber.

17. The method of claim 15, wherein the coating of the surfaces of the plurality of cage bodies is performed at a pressure of $3*10^{-3}$ to $7*10^{-3}$ torr, a temperature of 100 to 300° C., a power of 20 kW, and a voltage of 5 to 30 V.

* * * * *